(12) United States Patent
Tawwater et al.

(10) Patent No.: US 11,027,193 B2
(45) Date of Patent: Jun. 8, 2021

(54) TWO-ENVIRONMENT GAME PLAY SYSTEM

(71) Applicant: FLYINGTEE TECH, LLC, Jenks, OK (US)

(72) Inventors: Ryan S. Tawwater, Oklahoma City, OK (US); John M. Vollbrecht, Oklahoma City, OK (US); James T. Vollbrecht, Oklahoma City, OK (US)

(73) Assignee: FLYINGTEE TECH, LLC, Tulsa, OK (US)

( * ) Notice: Subject to any disclaimer, the term of this patent is extended or adjusted under 35 U.S.C. 154(b) by 0 days.

(21) Appl. No.: 14/819,999

(22) Filed: Aug. 6, 2015

(65) Prior Publication Data

US 2016/0001158 A1 Jan. 7, 2016

Related U.S. Application Data

(63) Continuation-in-part of application No. 14/321,333, filed on Jul. 1, 2014, now abandoned.
(Continued)

(51) Int. Cl.
*A63F 13/245* (2014.01)
*A63B 69/36* (2006.01)
(Continued)

(52) U.S. Cl.
CPC ........ *A63F 13/245* (2014.09); *A63B 24/0003* (2013.01); *A63B 24/0021* (2013.01);
(Continued)

(58) Field of Classification Search
CPC ............ A63B 24/0021; A63B 24/0025; A63B 24/0028; A63B 24/0037; A63B 24/004;
(Continued)

(56) References Cited

U.S. PATENT DOCUMENTS 4,137,566 A 1/1979 Haas et al.
4,283,056 A * 8/1981 Miller ................ A63B 69/3697
473/151

(Continued)

FOREIGN PATENT DOCUMENTS

CA 2839362 10/2012
WO 2007037705 4/2007
WO 2011065804 6/2011

OTHER PUBLICATIONS

Search Report for PCT Application No. PCT/US2014045109 dated Nov. 7, 2014.
(Continued)

*Primary Examiner* — Jeffrey S Vanderveen
(74) *Attorney, Agent, or Firm* — Crowe & Dunlevy, P.C.

(57) ABSTRACT

A game-play environment includes a tee box, a range surface, and a monitor. The tee box is configured to permit a player to hit a golf ball onto the range surface. The range surface has a plurality of physical markers. The monitor depicts a virtual environment that includes a plurality of virtual components. Some of the virtual components are visual cues that correspond to the physical markers. A player is able to play the game by targeting the appropriate physical marker that corresponds to the desired visual cue.

22 Claims, 11 Drawing Sheets

Related U.S. Application Data (60) Provisional application No. 61/841,544, filed on Jul. 1, 2013.

(51) Int. Cl.
| | | |
|---|---|---|
| *A63B 24/00* | (2006.01) | |
| *A63F 13/98* | (2014.01) | |
| *A63F 13/573* | (2014.01) | |
| *G16H 20/30* | (2018.01) | |
| *A63B 102/32* | (2015.01) | |

(52) U.S. Cl.
CPC ........ *A63B 69/3691* (2013.01); *A63F 13/573* (2014.09); *A63F 13/98* (2014.09); *G16H 20/30* (2018.01); *A63B 2024/0031* (2013.01); *A63B 2102/32* (2015.10); *A63B 2220/05* (2013.01); *A63B 2220/803* (2013.01)

(58) Field of Classification Search
CPC ............ A63B 24/0043; A63B 24/0034; A63B 24/0031; A63B 2220/806; A63B 69/36; A63B 69/3658; A63B 69/3691; A63B 69/3694
USPC .......................................... 473/168, 150–156
See application file for complete search history.

(56) References Cited

U.S. PATENT DOCUMENTS

| | | | |
|---|---|---|---|
| 4,673,183 | A | 6/1987 | Trahan |
| 5,092,602 | A | 3/1992 | Witler et al. |
| 5,150,895 | A | 9/1992 | Berger |
| 5,246,232 | A | 9/1993 | Eccher et al. |
| 5,290,037 | A | 3/1994 | Witler et al. |
| 5,303,924 | A * | 4/1994 | Kluttz ................ A63B 24/0021 473/155 |
| 5,342,051 | A | 8/1994 | Rankin et al. |
| 5,375,832 | A | 12/1994 | Witler et al. |
| 5,398,936 | A | 3/1995 | Kluttz et al. |
| 5,401,026 | A | 3/1995 | Eccher et al. |
| 5,413,345 | A | 5/1995 | Nauck |
| 5,486,002 | A | 1/1996 | Witler et al. |
| 5,489,099 | A | 2/1996 | Rankin et al. |
| 5,653,642 | A | 8/1997 | Bonacorsi |
| 5,700,204 | A | 12/1997 | Teder |
| 5,743,815 | A | 4/1998 | Helderman |
| 5,820,496 | A | 10/1998 | Bergeron |
| 5,879,246 | A | 3/1999 | Gebhardt et al. |
| 6,012,987 | A | 1/2000 | Nation |
| 6,179,720 | B1 | 1/2001 | Rankin et al. |
| 6,217,444 | B1 * | 4/2001 | Kataoka .................. A63F 13/10 434/252 |
| 6,304,665 | B1 | 10/2001 | Cavallaro et al. |
| 6,320,173 | B1 | 11/2001 | Vock et al. |
| 6,322,455 | B1 | 11/2001 | Howey |
| 6,371,862 | B1 | 4/2002 | Reda |
| 6,373,508 | B1 | 4/2002 | Moengen |
| 6,409,607 | B1 | 6/2002 | Libit et al. |
| 6,437,559 | B1 | 8/2002 | Zajac et al. |
| 6,520,864 | B1 | 2/2003 | Wilk |
| 6,547,671 | B1 | 4/2003 | Mihran |
| 6,607,123 | B1 | 8/2003 | Jollifee et al. |
| 6,702,292 | B2 | 3/2004 | Takowsky |
| 6,764,412 | B2 | 7/2004 | Gobush et al. |
| 6,781,621 | B1 | 8/2004 | Gobush et al. |
| 6,898,971 | B2 | 5/2005 | Dilz, Jr. |
| 6,905,339 | B2 | 6/2005 | DiMare et al. |
| 6,974,391 | B2 | 12/2005 | Ainsworth et al. |
| 6,998,965 | B1 | 2/2006 | Luciano, Jr. et al. |
| 7,040,998 | B2 | 5/2006 | Jolliffe et al. |
| 7,052,391 | B1 | 5/2006 | Luciano, Jr. |
| 7,059,974 | B1 | 6/2006 | Golliffe et al. |
| 7,095,312 | B2 | 8/2006 | Erario et al. |
| 7,143,639 | B2 | 12/2006 | Gobush |
| 7,160,196 | B2 | 1/2007 | Thirkettle et al. |
| 7,214,138 | B1 | 5/2007 | Stivers et al. |
| 7,223,169 | B2 | 5/2007 | Imaeda et al. |
| 7,317,388 | B2 | 1/2008 | Kawabe et al. |
| 7,321,330 | B2 | 1/2008 | Sajima |
| 7,337,965 | B2 | 3/2008 | Thirkettle et al. |
| 7,344,446 | B2 | 3/2008 | Wyeth |
| 7,497,780 | B2 | 3/2009 | Kiraly |
| 7,641,565 | B2 | 1/2010 | Kiraly |
| 7,787,886 | B2 | 8/2010 | Markhovsky et al. |
| 7,815,516 | B1 | 10/2010 | Mortimer et al. |
| 7,822,424 | B2 | 10/2010 | Markhovsky et al. |
| 7,837,572 | B2 | 11/2010 | Bissonnette et al. |
| 7,843,429 | B2 | 11/2010 | Pryor |
| 7,854,669 | B2 * | 12/2010 | Marty ................ A63B 69/0071 473/467 |
| 8,018,375 | B1 | 9/2011 | Alexopoulos et al. |
| 8,068,095 | B2 | 11/2011 | Pryor |
| 8,077,917 | B2 | 12/2011 | Forsgren |
| 8,113,964 | B2 | 2/2012 | Lindsay |
| 8,142,302 | B2 | 3/2012 | Balardeta et al. |
| 8,257,189 | B2 | 9/2012 | Koudele et al. |
| 8,328,653 | B2 | 12/2012 | Lock |
| 8,335,345 | B2 | 12/2012 | White et al. |
| 8,400,346 | B2 | 3/2013 | Hubbard et al. |
| 8,409,024 | B2 | 4/2013 | Marty et al. |
| 2005/0227792 | A1 | 10/2005 | McCreary et al. |
| 2007/0078018 | A1 * | 4/2007 | Kellogg ............. A63B 24/0021 473/151 |
| 2007/0293331 | A1 | 12/2007 | Tuxen |
| 2008/0139330 | A1 | 6/2008 | Tuxen |
| 2008/0261711 | A1 | 10/2008 | Tuxen |
| 2009/0036237 | A1 | 2/2009 | Nipper et al. |
| 2009/0295624 | A1 | 12/2009 | Tuxen |
| 2010/0137079 | A1 | 6/2010 | Burke et al. |
| 2011/0077093 | A1 * | 3/2011 | Garratt ................ A63B 69/3658 473/131 |
| 2011/0230986 | A1 | 9/2011 | Lafortune et al. |
| 2011/0286632 | A1 | 11/2011 | Tuxen et al. |
| 2012/0068879 | A1 | 3/2012 | Tuxen |
| 2013/0039538 | A1 | 2/2013 | Johnson et al. |
| 2013/0084930 | A1 | 4/2013 | Chang et al. |
| 2013/0274025 | A1 * | 10/2013 | Luciano, Jr. ....... A63B 69/3658 473/156 |
| 2016/0287967 | A1 * | 10/2016 | Baldwin ............ A63B 24/0021 |

OTHER PUBLICATIONS

Application No. 14819897.1-1905, Extended European Search Report, dated Jan. 20, 2017.
European Application No. 14819897.1-1209, EPO Communication pursuant to Article 94(3) EPC dated Oct. 8, 2018.
Chinese Patent Application No. 201480037296.2, SIPO Third Office Action dated Dec. 29, 2017.
Chinese Patent Application No. 201480037296.2, Response to Third Office Action dated May 14, 2018 (Chinese).
Chinese Patent Application No. 201480037296.2, Response to Third Office Action dated May 14, 2018 (English).

* cited by examiner

TWO-ENVIRONMENT GAME PLAY SYSTEM

PRIORITY CLAIM

This U.S. Non Provisional Patent Application claims priority from, and is a continuation in part of, U.S. patent application Ser. No. 14/321,333, filed on Jul. 1, 2014 with the same title and inventors as the present application. That application claims the benefit of U.S. Provisional Patent Application No. 61/841,544, filed on Jul. 1, 2013 with the same title and inventors as the present application.

This invention relates to a system and method related to a game play environment.

BACKGROUND OF THE INVENTION

Conventional methods of tracking an object (e.g. golf ball, basketball, baseball, etc.) employ various types of sensors including Doppler radar technology, camera based technology, high speed 3D camera based technology, and stereoscopic sensors. The sensors can be configured to track the object and with the aid of a computer can recreate the movement of the object in a computerized virtual environment. In athletic application, these tracking systems have been used to provide feedback for coaching, player development, and other training/improvement applications, with focus on the movement of a virtual object relative to a virtual environment. The prior art is principally focused on providing analysis about the player's technique and the resulting effect on the flight path of the object. These systems have found a particular benefit in the area of golf instruction.

Conventional indoor golf simulators utilize sensors, as mentioned above, to represent data points in a virtual space, which are projected onto a screen into which the golf ball is hit. Such simulators monitor the initial flight of the ball with sensors, which extrapolate the full flight of the ball and relay those data points to a computer system that creates a representation of the data points in a virtual space, such as a virtualized hole on a golf course. The prior art focuses on capturing the data points and incorporating the data points into a predominately virtual environment, with no identifiable links to the physical environment where the golf ball was actually hit.

It is apparent that there is a need for a system and method of tracking a ball, or other object, and rendering the flight path of that ball in a virtual gaming environment that is coordinated with the physical environment in which the ball is struck as well as providing games and results based on various targets within the physical or virtual environment. Additionally, there is the need to alter the game play environment that the user experiences without changing the physical environment into which the ball or object is hit and to use sensors to track the entire flight of the ball in the actual physical environment. The present invention is focused on solving such a need and providing the techniques thereby to fulfill these needs.

BRIEF SUMMARY OF THE INVENTION

Described herein is a game-play environment that includes a tee box, a range surface, and a monitor. The tee box is configured to allow a player to hit a golf ball onto the range surface. The range surface has a plurality of physical markers. The monitor is positioned so that the player can see the monitor while in the tee box. The monitor depicts a virtual environment that corresponds to a desired virtual game. Depending on the particular game selected, a set of virtual components are displayed on the monitor. Some of these virtual components are visual cues that correspond to the physical markers on the range surface. The player can achieve the game's objectives by targeting the appropriate physical marker that corresponds to the desired visual cue.

DETAILED DESCRIPTION OF THE INVENTION

Figure 1:
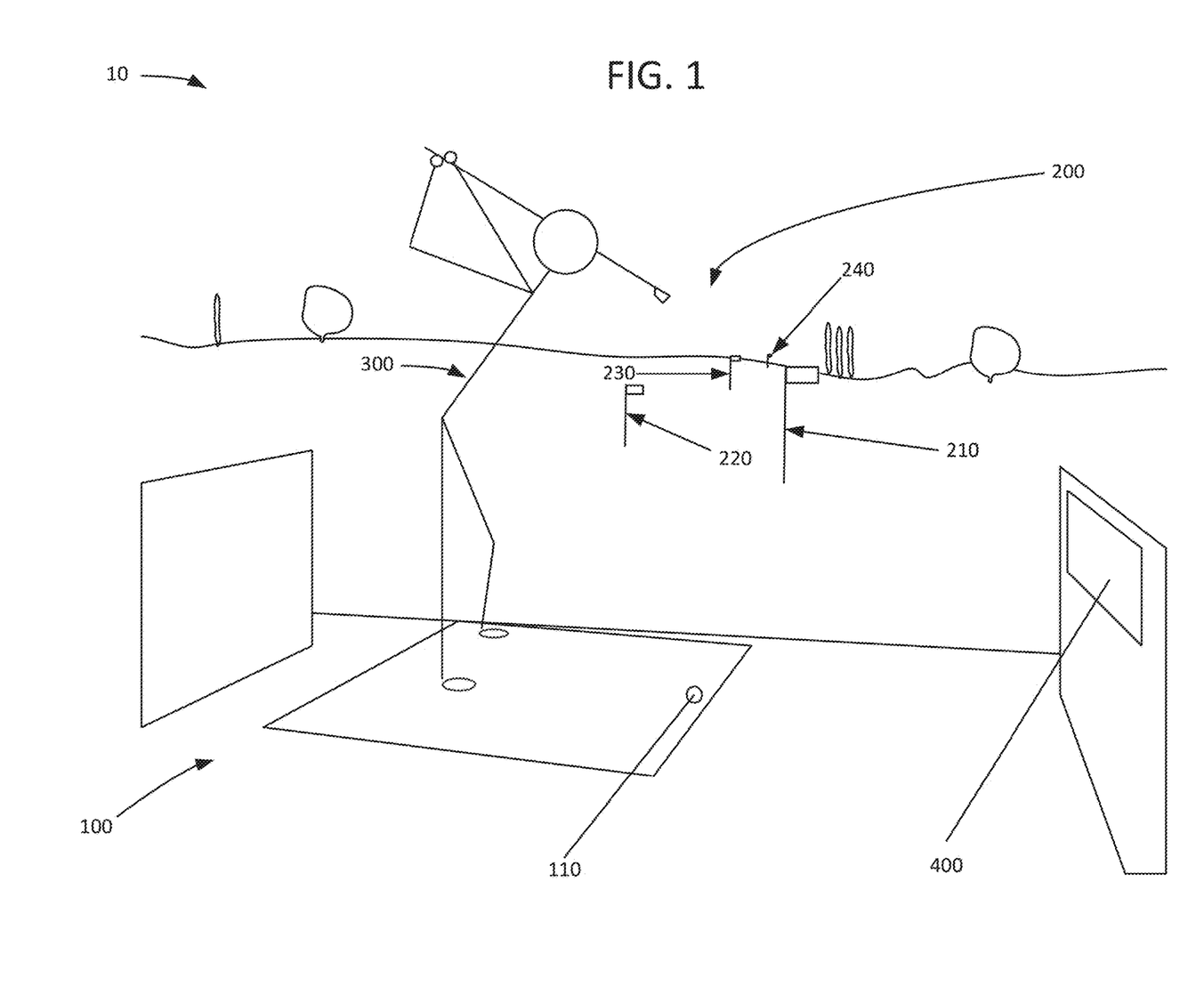
FIG. 1 depicts a perspective view of a physical environment that is used in the game play.

In accordance with a preferred embodiment of the present invention, a game-play environment 10 includes a tee box 100 and a range surface 200. The tee box 100 includes a ball 110 and a monitor 400. The range surface 200 includes a plurality of physical markers 210, 220, 230, and 240. FIG. 1 is a perspective view of a preferred embodiment of the game-play environment 10. Shown therein is a player 300 positioned in the tee box 100 over the golf ball 110 and facing the monitor 400. It is understood that the particular position of the player 300 within the tee box 100 enables that player 300 to see the physical markers 210, 220, 230, and 240 and also to see the monitor 400. It will be further understood that while FIG. 1 depicts a preferred embodiment of the game-play environment 10, other embodiments and arrangements of the constituent parts of the game-play environment 10 are possible. For example, the monitor 400 can be raised or mounted on a standard pivot mount for adjustable positioning within the tee box 100. Similarly, the positioning of the plurality of physical markers on the range surface 200 can be adjusted as desired for a particular embodiment. It is preferred, however, that the plurality of physical markers generally be distributed throughout the range surface 200 to facilitate game play, as discussed below. In the preferred embodiment, the physical markers are distributed throughout the range surface 200 at distances of approximately 60 yards, 130 yards, 180 yards, and 210 yards from the tee box 100.

Figure 2:
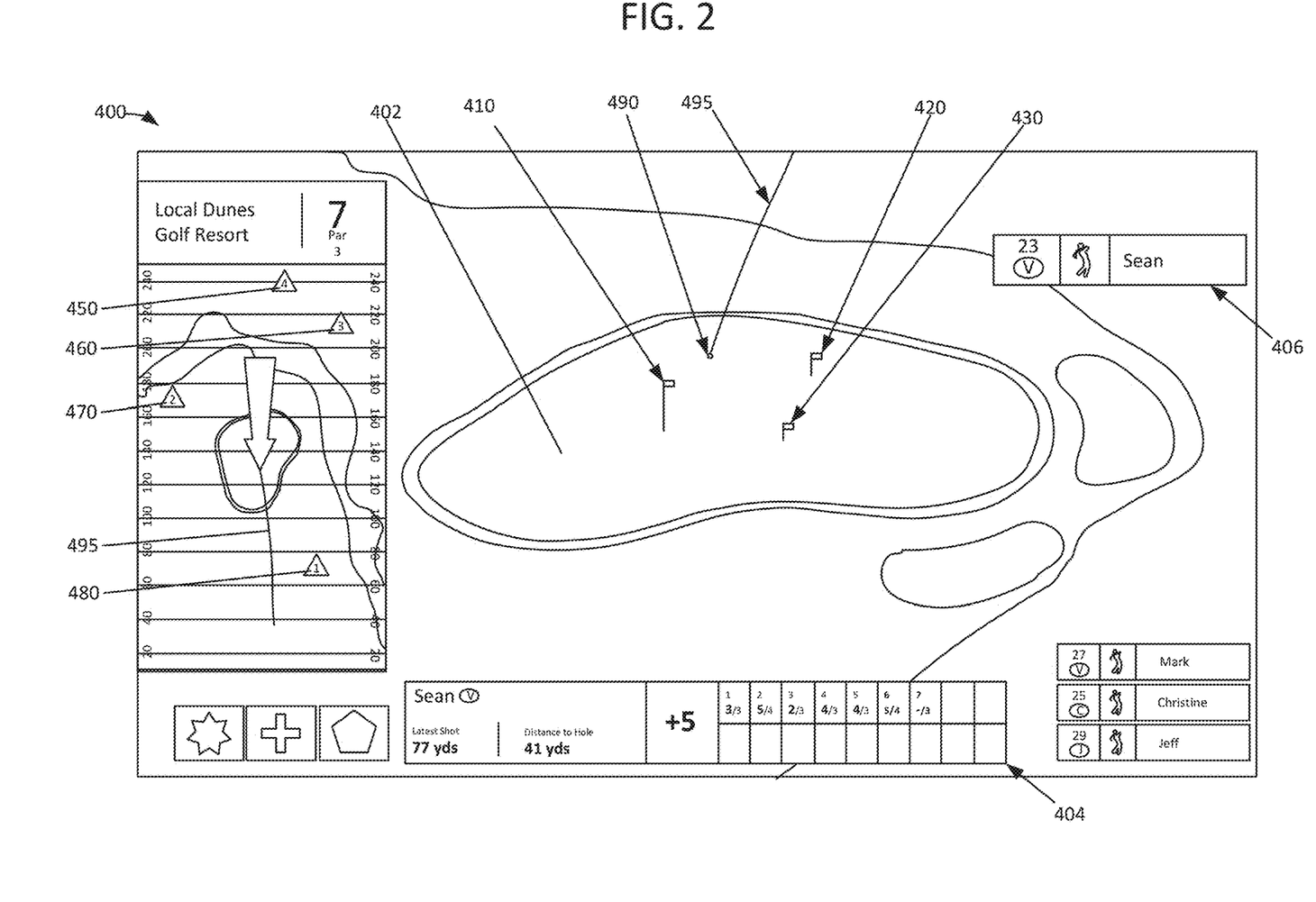
FIG. 2 depicts a side perspective view of a virtual environment showing the path a ball travels through that virtual environment.

Turning to FIG. 2, depicted therein is a virtual environment that is displayed to the player 300 on the monitor 400. In the preferred embodiment, the virtual environment 10 is configured to play a virtual game of golf. Accordingly, the virtual environment shown in FIG. 2 consists of a plurality of visual components appropriate for a golf game, including without limitation, a golf green 402, a player score card 404, a current player information box 406, a plurality of player location flags 410, 420, and 430, a plurality of visual cues 450, 460, 470, and 480, a virtual golf ball 490, and a golf ball flight path 495.

Some of these visual components correspond with physical aspects of the range surface 200 and tee box 100. For example, the visual cues 450, 460, 470, and 480 correspond with the physical markers 210, 220, 230, and 240 respectively. Importantly, the relative positions and distances between the physical markers 210, 220, 230, and 240 are the same relative positions and distances depicted between the visual cues 450, 460, 470, and 480. It will be understood that by depicting a plurality of visual cues in the virtual environment that correspond to a plurality of physical markers on the range surface 200, various desirable features of the golf game become possible. It will be further understood that other games can benefit from the correspondence of physical markers with visual cues, including without limitation baseball, football, ultimate frisbee, tennis, and others.

One such benefit is that after a player 300 strikes the golf ball 110, the place that the golf ball 110 comes to rest on the range surface 200 can be depicted within the virtual environment as being in a position and distance from each of the plurality of visual cues that corresponds to position and distance of the golf ball 110 from each of the plurality of physical markers on the range surface. For example, if the resting place of the golf ball 110 is 10 feet north of physical marker 220, 15 feet west of physical marker 230, and 40 feet south of physical marker 240, the monitor 400 will display a virtual golf ball 490 as being 10 feet north of visual cue 450, 15 feet west of visual cue 460, and 40 feet south of 470.

Another benefit of depicting a plurality of visual cues in the virtual environment that correspond to a plurality of physical markers on the range surface 200, is that the actual path that the golf ball 110 travels from the tee box 110 to the range surface 200 can be depicted within the virtual environment and displayed on the monitor 400. FIG. 2 depicts this path 495.

Figure 4A:
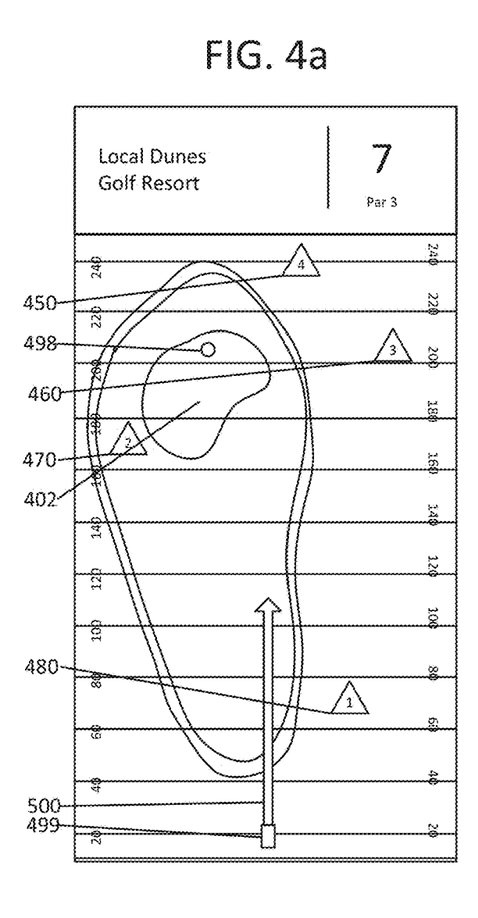
FIG. 4a depicts a top view of a second preferred embodiment of a virtual environment.

Yet another benefit of depicting a plurality of visual cues in the virtual environment that correspond to a plurality of physical markers on the range surface 200 is that the player 300 can use the plurality of physical markers as targets that correspond to particular visual components depicted within the virtual environment. For example turning to FIG. 4a, if in the particular game being played in the game-play environment 10 it is desirable to get the virtual golf ball 490 to rest near visual component 498 (which his depicted as the cup on a golf hole), then the player 300 can adjust his golf shot (by changing golf clubs, stroke mechanics, foot position, body position, etc.) to improve the chances that the golf ball 110 will come to rest near physical marker 210, which corresponds to visual cue 450, the visual cue closest to visual component 498.

Figure 4B:
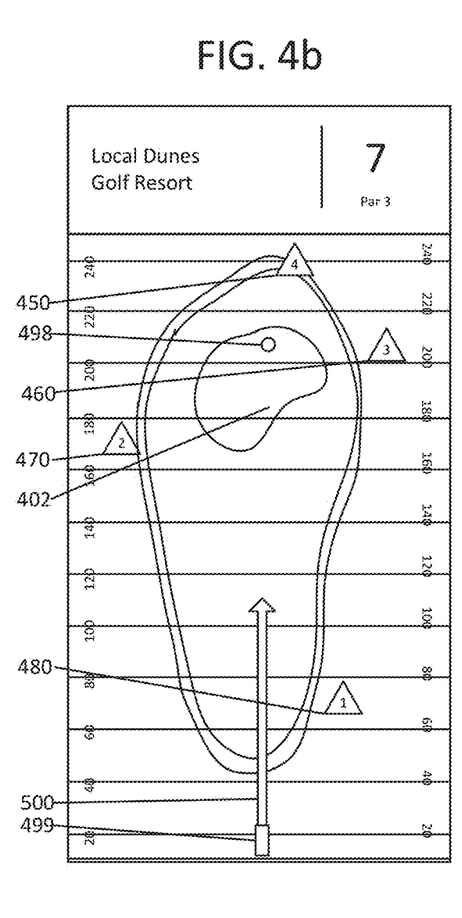
FIG. 4b depicts a top view of the second preferred embodiment from FIG. 4a wherein the virtual environment has been adjusted for aiming.
Figure 4C:
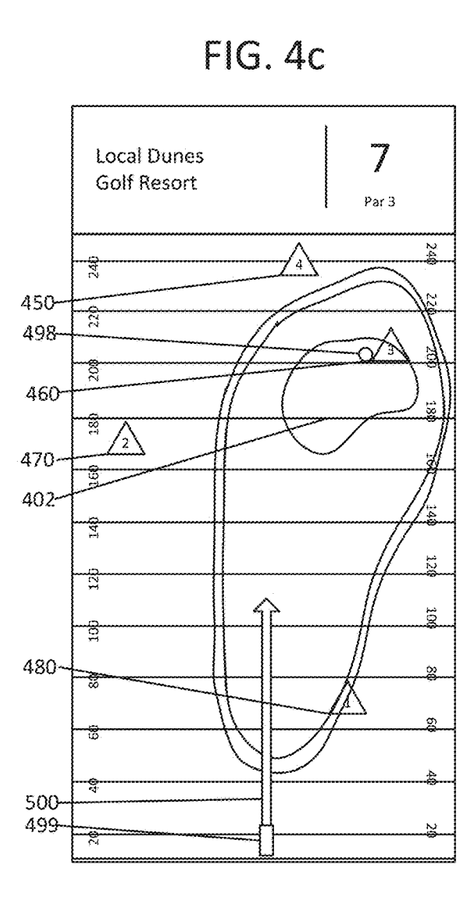
FIG. 4c depicts a top view of the second preferred embodiment from FIGS. 4a & 4b wherein the virtual environment has been further adjusted for aiming.

It will be understood that the virtual environment may also be adjusted so that the visual cues 450, 460, 470, and 480 that correspond to physical markers 210, 220, 230, and 240 are better aligned with the desired visual components. For example, FIG. 4b depicts the same virtual environment of FIG. 4a, except that the perspective has been selectively rotated so that visual cue 460 is now in closer proximity to visual component 498. FIG. 4c shows that the perspective can be adjusted even further bring in visual cue 460 is even closer proximity to visual component 498. Thus, the player 300 may now improve their chances of getting the virtual golf boll 490 to rest near visual component 498 by aiming their golf shot at physical marker 220, which corresponds to visual cue 460.

It will be further understood that other visual components can be displayed to assist the player 300 in aiming. For example, in FIGS. 4a, 4b and 4c, a virtual tee box 499 is shown, which corresponds to the tee box 100, and a directional indicator 500 is displayed to indicate in what direction the virtual golf ball 490 will travel if the player 300 hits the golf ball 110 on a heading of 0 degrees (directly straight down the range surface 200).

Figure 3:
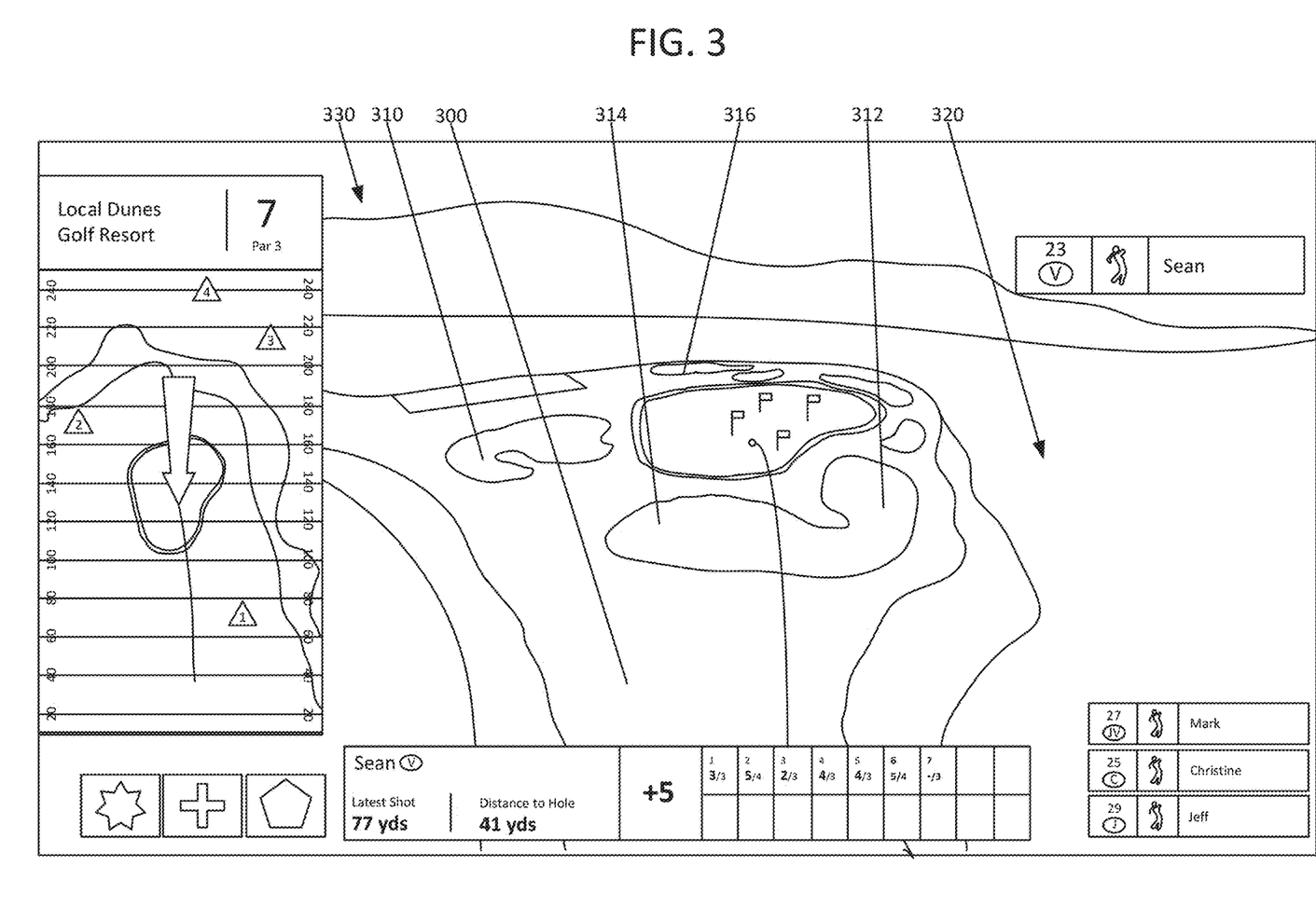
FIG. 3 depicts a front perspective view of a first preferred embodiment of a virtual environment.

It will be understood that other visual components appropriate to a golf game, if desired, may be used in the preferred embodiment, including without limitation fairways, sand traps, virtual tee boxes, water hazards, and out of bounds markers. In addition, it may be desirable to include other visual components to be depicted within the virtual environment that do not necessarily affect the play of the virtual golf game, but rather fill the background of the virtual environment, including without limitation, rivers, lakes, houses and other structures, mountains, trees, oceans, cliffs, clouds, and other weather-related constructs. FIG. 3 depicts another preferred embodiment of the virtual environment depicted on the monitor 400, which includes a fairway [300], a plurality of sand traps 310, 312, 314, 316 an ocean 320, mountains 330, and other non-enumerated visual components.

Turning back to FIG. 1, the preferred golf game begins by having the player 300 look at the monitor 400 to determine where they should aim their first golf shot. The virtual environment depicted on the monitor 400 will initially show the virtual golf ball 490 in a virtual tee box of a golf hole (corresponding to the actual golf ball 110 within the actual tee box 100). Depending on the particular shape and length of the fairway of the virtual golf hole depicted within the virtual environment, the player 300 will select a strategy to get his virtual golf ball into the cup on the green of the golf hole using the fewest golf shots. This strategy may involve selecting a particular golf club and striking the golf ball 110 in the tee box 100 thereby causing the golf ball 110 to fly through the air on a particular path onto the range surface 200. That path 495 will be depicted within the virtual environment and shown on the monitor 400. The monitor may then redraw the virtual environment to show the new position of the virtual golf ball 490. Play will continue with the player 300 iteratively targeting a desired physical marker, taking a golf shot, and then watching the monitor draw the path 495 of the virtual golf ball 490 that corresponds to the flight path of the actual golf ball 110 relative to the plurality of physical markers.

It is understood that the various embodiments of the game have different objectives and goals. In a preferred embodiment, the objective is to get the virtual golf ball 490 to the cup on the golf green 498 taking the fewest number of golf shots possible.

Figure 5:
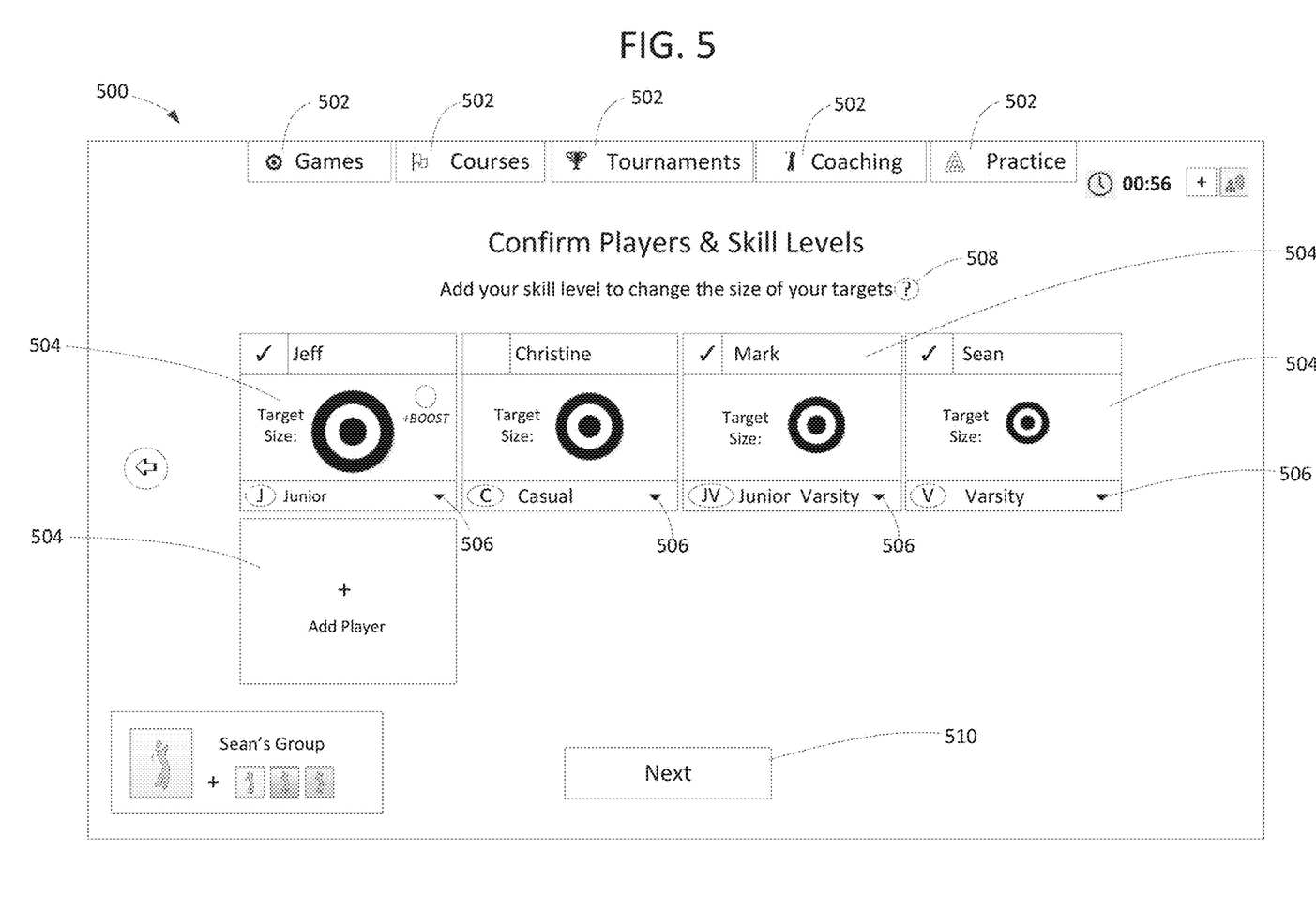
FIG. 5 depicts a preferred embodiment of a game setup screen for a gaming system for use with the virtual environment.

Turning now to FIG. 5, depicted therein is an embodiment of a game setup screen 500 for a virtual golf game which may be depicted on the monitor 400. The game setup screen 500 may include a plurality of selectable menu items 502, a plurality of player boxes 504 each containing a drop down menu 506 for selecting a skill level, a target size help menu 508 and a next button 510. In a preferred embodiment, the monitor 400 is a touch screen monitor; however it will be understood that the monitor 400 could also use a mouse, track pad or be configured so that hand gestures or movements are detected.

The plurality of selectable menu items 502 allow a player of the virtual golf game to select the desired virtual environment they wish to encounter during their play time. Each of the virtual environments are displayed to the user on a screen or monitor and are imposed virtually onto the physical range, which allows the physical range to remain unchanged and present a variety of virtual environments to the player(s). The plurality of selectable menu items 502 may include, but is not limited to virtual golf games, courses, tournaments, coaching levels and practice environments.

Each of the selectable menu items 502 may include a variety of options which may be selected to determine the desired virtual environment. For example, the selectable menu item 502 entitled "Games" may include the virtual game of golf described above, card games such as 21 or poker, darts, long drive, HORSE, and the like. By way of further example, the selectable menu item 502 entitled "Courses" may include a list of golf courses with different environments and topography which may be selected. The selectable menu item 502 entitled "Tournaments" may include a list of various contests, or special instances of a game or golf course, in which there are a limited number of players or entries allowed, and within which players can earn rewards for earning the best score. The selectable menu item 502 entitled "Coaching" may provide a list of various coaching modules to select, such as distance training, use of various clubs, swing modification, etc. Also, the selectable menu item 502 entitled "Practice" may provide a list of practice courses, clubs, greens, distances and other variables which may be selected.

Figure 6:
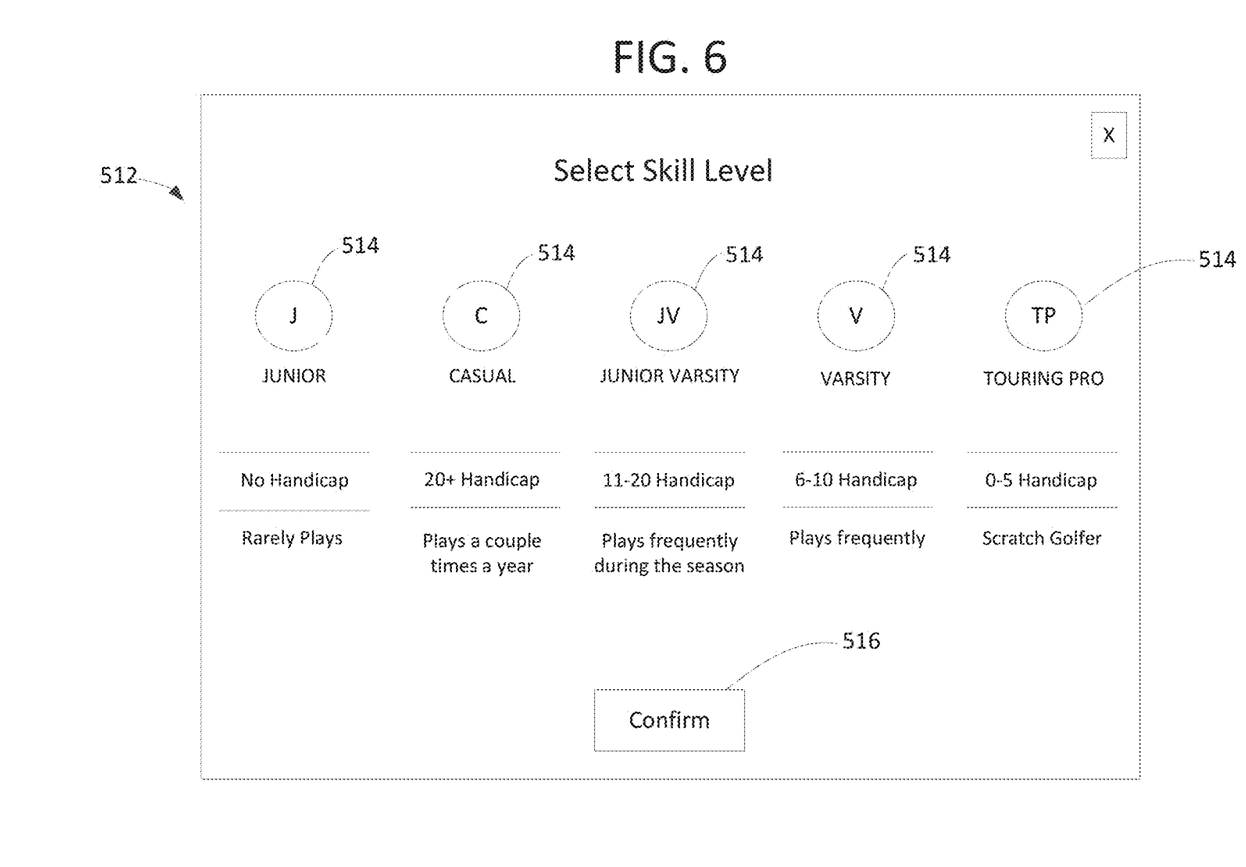
FIG. 6 depicts a preferred embodiment of a skill select screen for selection of skill level within the gaming system.

The game setup screen 500 also allows additional players and player information to be added, deleted, or revised by selecting from the plurality of player boxes 504. Additionally, the skill level of a particular player may be added or changed by selecting the drop down menu 506 associated with a particular player box 504. Referring to FIG. 6, shown therein is a skill level select screen 512 which is presented on the monitor 400 when the drop down menu 506 associated with a particular player box 504 is selected. The skill level select screen 512 includes a plurality of skill levels 514 that may be associated with a particular player which may be selected. It will be understood by those skilled in the art that the selection of the appropriate skill level for a particular player can be based on a wide variety of skills, such as handicap, amount of playtime during a season, and other variables commonly used to determine skill level. Once the skill level is selected and the confirm button 516 pressed, the monitor 400 will present the game setup screen 500.

Figure 7A:
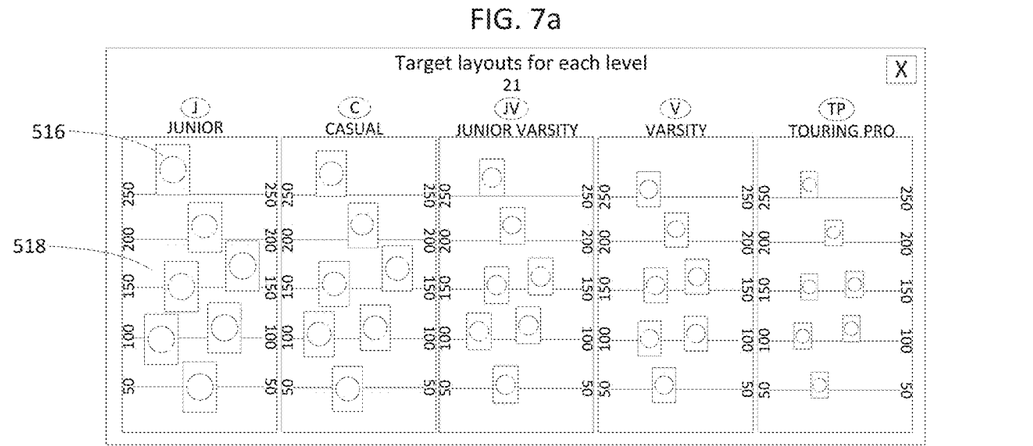
FIG. 7a depicts a preferred embodiment of a target layout screen of a card game for each skill level within the gaming system.
Figure 7B:
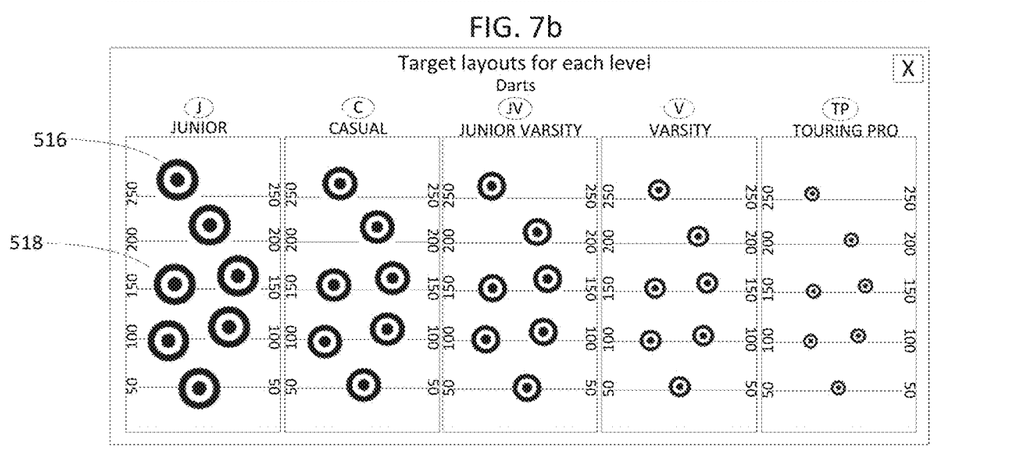
FIG. 7b depicts a preferred embodiment of a target layout screen of a dart game for each skill level within the gaming system.
Figure 7C:
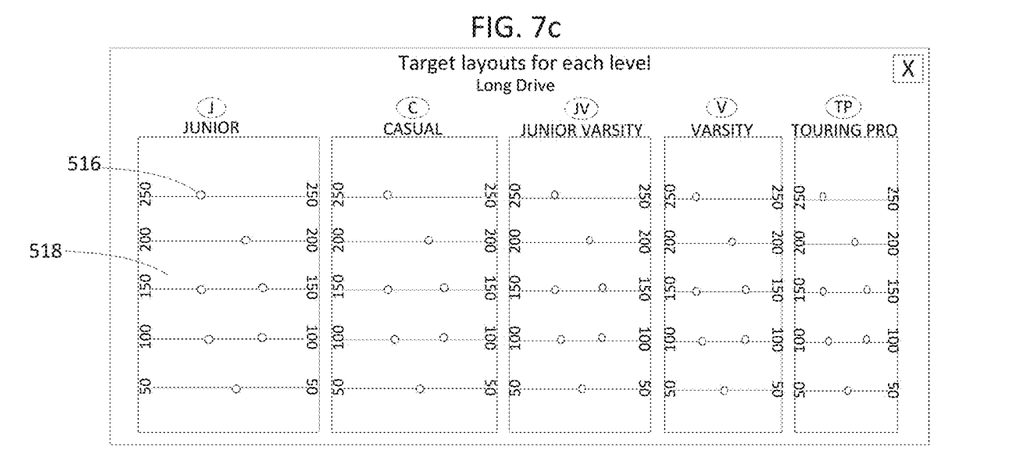
FIG. 7c depicts a preferred embodiment of a target layout screen of a longest drive game for each skill level within the gaming system.

Turning to FIGS. 7a, 7b, and 7c, depicted therein are the various target layouts which are presented if the target size help menu 508 from the game setup screen 500 is selected. The target layouts are shown based on the game selected from the selectable menu items 502 and may show target layouts for a variety of virtual games. FIG. 7a shows a target layout for a virtual card game 21. FIG. 7b shows a target layout for a virtual dart game. FIG. 7c shows a target layout for a virtual long drive game. It will be understood that numerous other target layouts could be shown for the particular games included in the selectable menu items 502, including games such as poker, HORSE, or other games adapted to the virtual environment.

Each of the target layouts in FIGS. 7a, 7b, and 7c depicts the size of the targets 516 and/or the size of the in-bounds area 518 for the course depending on the skill level selected in the skill level menu 512 for each skill level. As further shown in FIGS. 7a and 7b, the size of the targets 516 may vary based on the skill level selected, such that a lower skill level presents the player with larger targets for the player to hit within the virtual game. Additionally, as shown in FIG. 7c, the size of the in-bounds area may also vary based on the skill level selected, such that a lower skill level presents the player with a larger in-bounds area 518. It will be understood that numerous combinations and sizes may be use for each of the targets 516 and/or in-bounds areas 518 depending on the type of game or desired settings for each game.

Figure 8A:
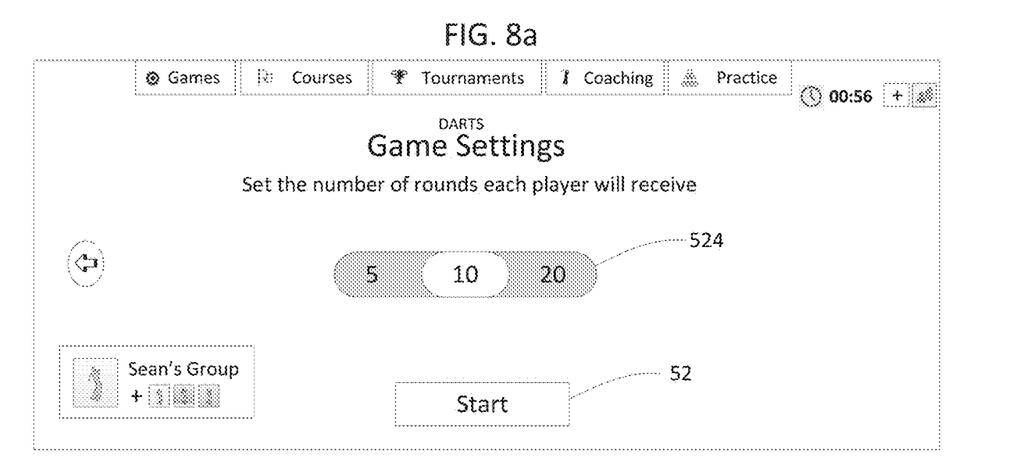
FIG. 8a depicts a preferred embodiment of a game settings selection screen for a dart game.
Figure 8B:
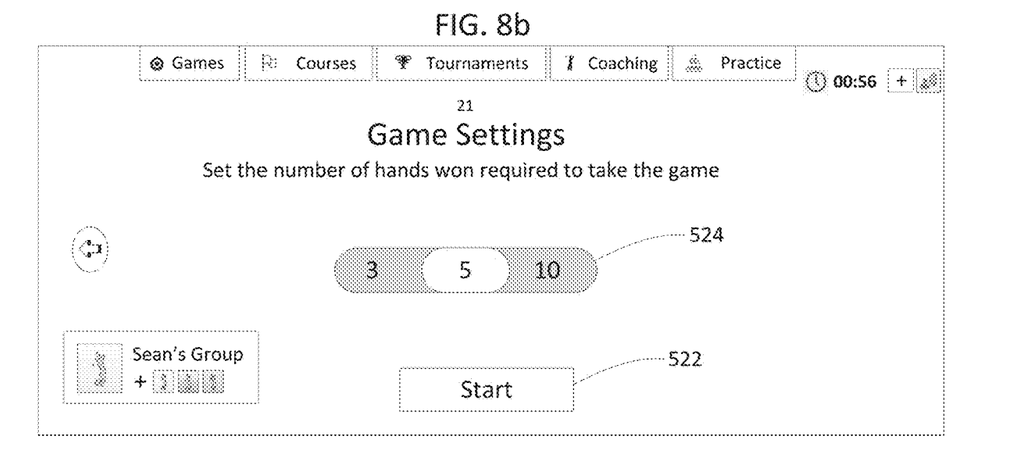
FIG. 8b depicts a preferred embodiment of a game settings selection screen for a card game.
Figure 8C:
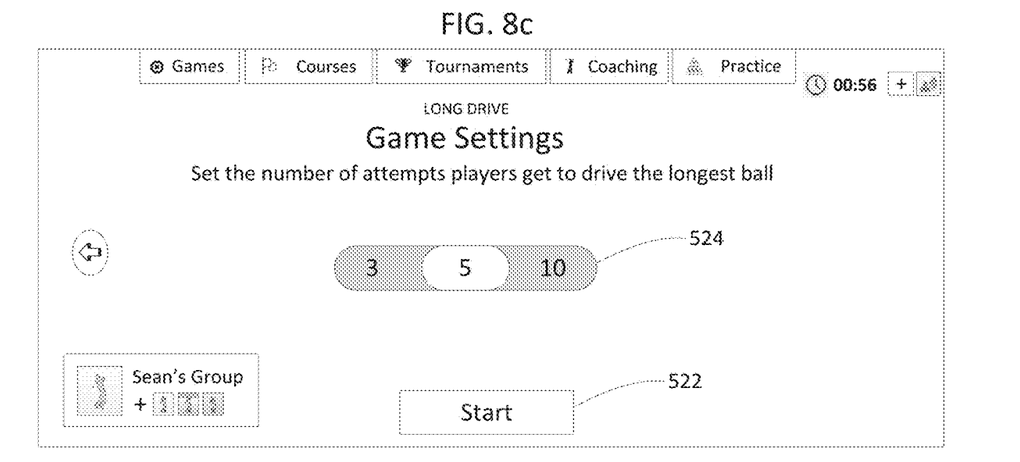
FIG. 8c depicts a preferred embodiment of a game settings selection screen for a longest drive game.

When the next button 510 from the game setup screen 500 is pressed, and a particular game has been selected from the plurality of selectable menu items 502, the screen will display a new screen showing the game settings for the game selected. Turning to FIGS. 8a, 8b, and 8c, depicted therein are various game setting screens 520 for a particular game. The game setting screens 520 may include a start button 522 and a settings selection box 524 for selecting the various shots, length of the game, or attempts the player may receive during the virtual game.

Figure 9:
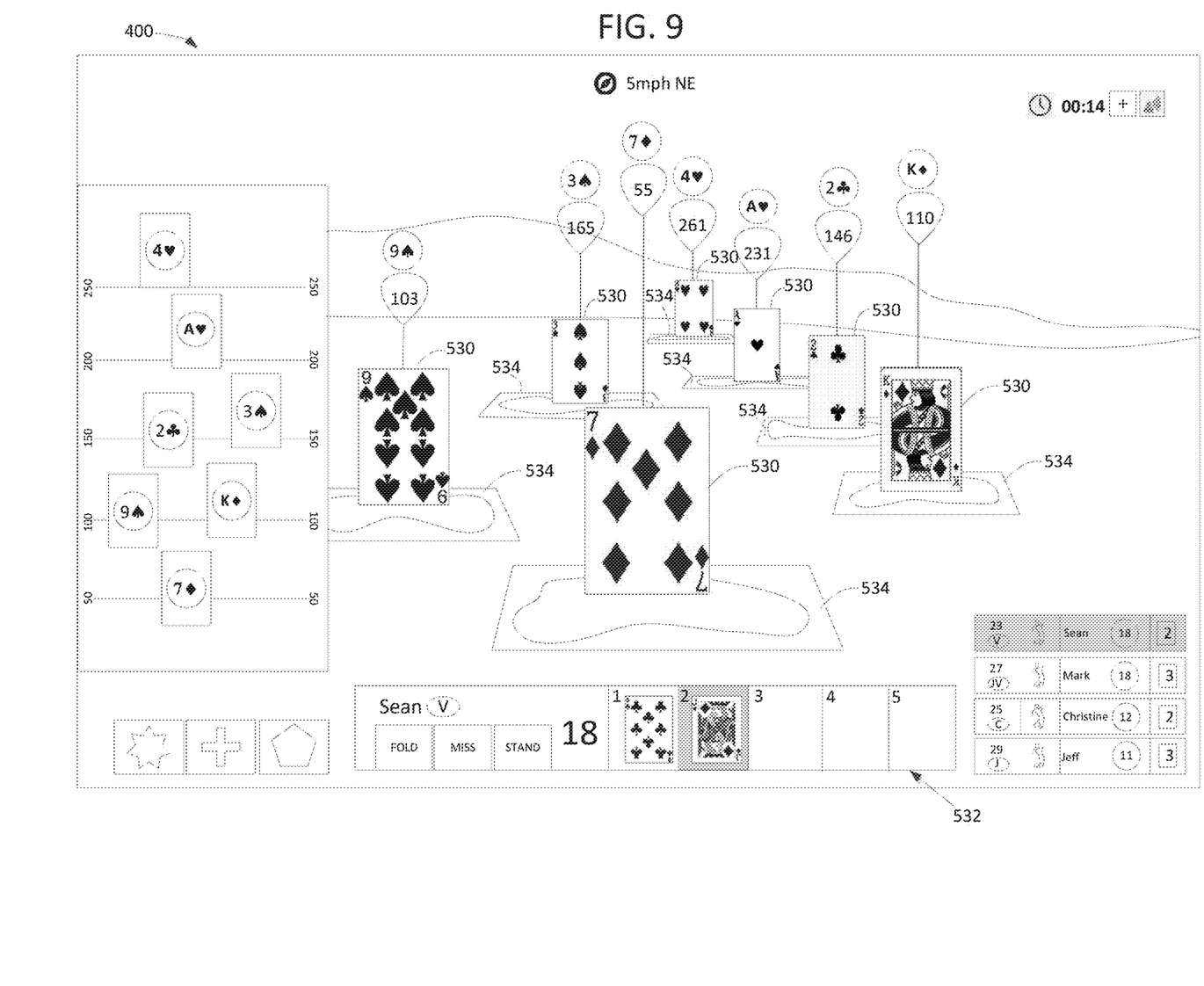
FIG. 9 depicts a front perspective view of a preferred embodiment of a virtual environment for a card game.

Turning now to FIG. 9, depicted therein is a preferred virtual environment for playing a blackjack card game. The virtual environment is displayed on the monitor 400. The virtual environment shown in FIG. 9 consists of a plurality of playing cards 530 and a player score card 532. The plurality of visual cards 530 are selected randomly from a pre-determined number of playing card decks with fifty-two (52) cards in each deal by a computer system and then assigned to various physical markers 534 within the virtual playing field. Although not depicted in FIG. 10, it will be understood that the playing field may also include an in-bounds and out-of-bounds area which may change size based on the skill level of the player. The player score card 532 shows the cards that have been hit by the player during each of that player's turns.

In the preferred embodiment, one or more players take turns trying to hit a particular playing card from the plurality of playing cards 540 with a sports ball to win the card or value assigned to the playing card. The players may take numerous turns to attempt to reach a certain total value, such as 21 for black jack, or the values necessary to win 3 card or 5 card poker, etc. After all of the players have made the set number of attempts, the system resolves the players' resulting hands against each other based on the rules and hand hierarchy as required by the game and then announces the winner to be the player with the best hand. For example, in Blackjack, or 21, the player with the points total closest to 21 without going over 21 wins. Additionally, in a preferred embodiment, if there is a tie, the tied players may be allowed to take another turn to attempt to hit the highest value card on the virtual playing field. In a preferred embodiment, if a player does not hit a card during a turn, the player may have the opportunity to draw a card from the cards remaining in the deck, which is randomly assigned by the computer system. In another preferred embodiment, the probability of drawing a card helpful to that player's hand can be weighted such that a player of higher skill is more likely to draw a card that is unhelpful, while a player of lower skill is more likely to draw a card that is helpful based on the cards in the player's hand during that turn.

Figure 10:
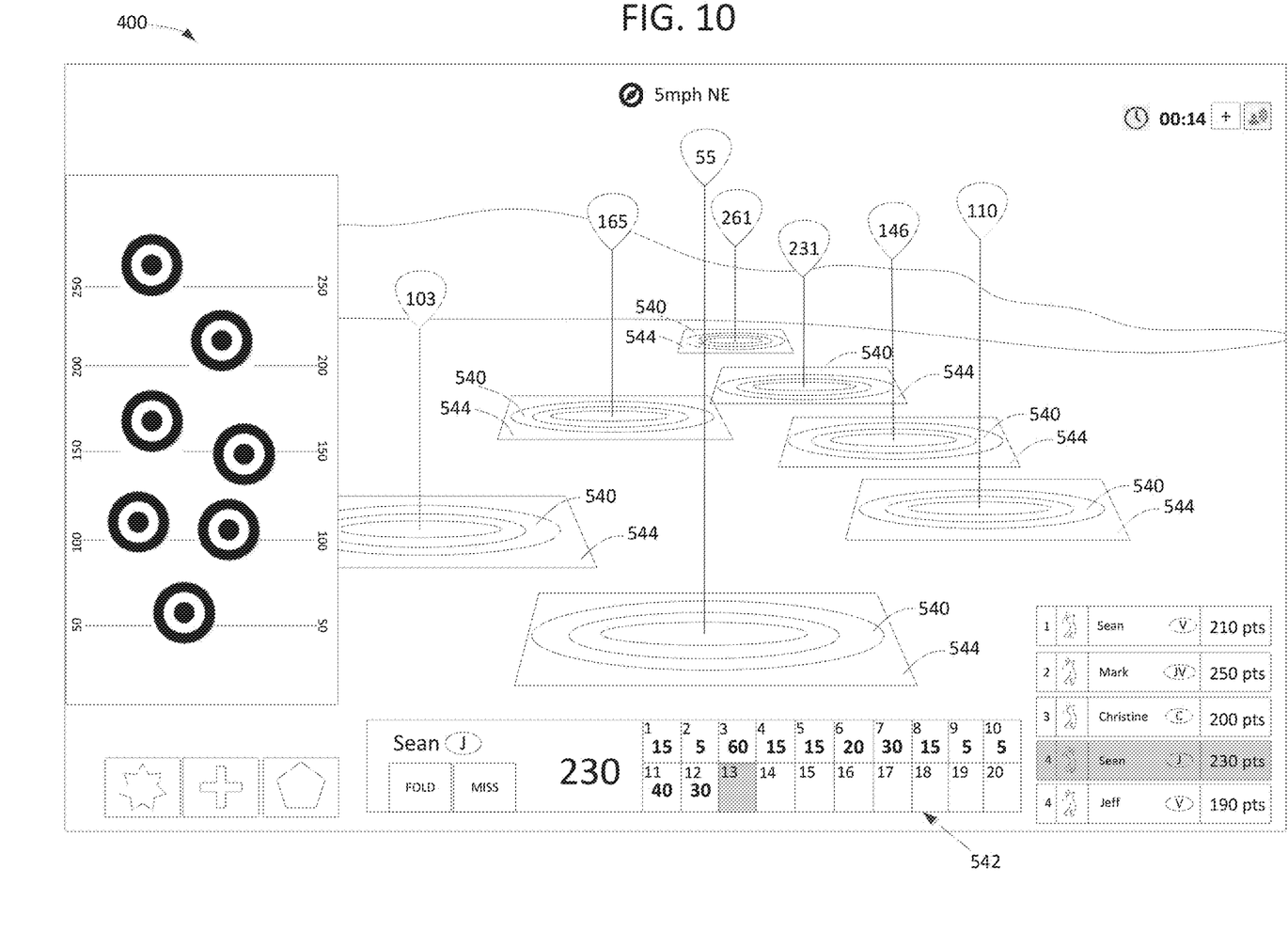
FIG. 10 depicts a front perspective view of a preferred embodiment of a virtual environment for a dart game.

Turning now to FIG. 10, depicted therein is a second preferred virtual environment that is displayed on the monitor 400. The second preferred embodiment is configured to play a game of darts. The virtual environment shown in FIG. 10 consists of a plurality of visual targets 540 and a player score card 542. The plurality of visual targets 540 are assigned to various physical markers 544 within the virtual playing field. It will be understood that although the visual targets 540 are shown as concentric rings, the visual targets 540 could be various shapes and sizes depending on the terrain of the selected target area or course. Further, although the physical markers 544 are depicted as rectangular in FIG. 10, it will be understood that the physical markers may be various shapes or not visible depending on the course selected. Although not depicted in FIG. 10, it will be understood that the playing field may also include an in-bounds and out-of-bounds area which may change size based on the skill level of the player. The player score card 542 shows the score that the player has earned during each round.

In the second preferred embodiment, one or more players take turns trying to hit a particular target from the plurality of visual targets 540 with a sports ball to win the value assigned to that target and/or the rings around the target. After all of the players have made the set number of attempts, the system resolves each player's resulting scores against the other player's scores by summing the total number of points for each player. Additionally, in a preferred embodiment, if there is a tie, the tied players may be allowed to take another turn to attempt to hit the highest value target on the virtual playing field. In a preferred embodiment, if a player misses all of the targets during a turn, the player may be awarded a minimum number of points based on the skill level of the player.

Although the plurality of visual targets 540 are shown in two dimensions, such that they are lying flat on the playing surface area on the X-Y axis, it will be understood that the plurality of visual targets 540 could also be displayed in three dimensions similar to the plurality of playing cards 530 in FIG. 9, such that they are standing in the air on the X, Y and Z axis. Additionally, it will be understood that the plurality of playing cards 530 in FIG. 9 could also be displayed in two dimensions similar to the plurality of visual targets 540 in FIG. 10. Alternatively, the visual targets 540 could be projected onto a retention net that borders the range surface 200.

Although FIGS. 9 and 10 display specific games of blackjack and darts respectively, it will be understood that a variety of games could be displayed and played based on the games available in the computer system, including long drive, poker, HORSE, and numerous other options. For example, in a third preferred embodiment, the game long drive is selected. The game is played so that each player takes turns trying to move the ball from that player's first position to the farthest possible position, wherein a farther landing place is equal to a higher point value. Each player takes a set number of attempts to advance the ball the farthest and the winner is the player whose final distance is the farthest away from the player's starting position. It will be understood that the size of the in-bounds and out-of-bounds area may change sizes based on the skill of the player such that players with higher levels of skills will be presented with a smaller in-bounds area than those of a lower skill level.

It will also be understood that although the virtual environment shown in FIGS. 9 and 10 are depicted on the monitor 400, the virtual environment could also be projected in front of the player, such as using a virtual reality display device, such as Google glass or other similar devices.

Figure 11:
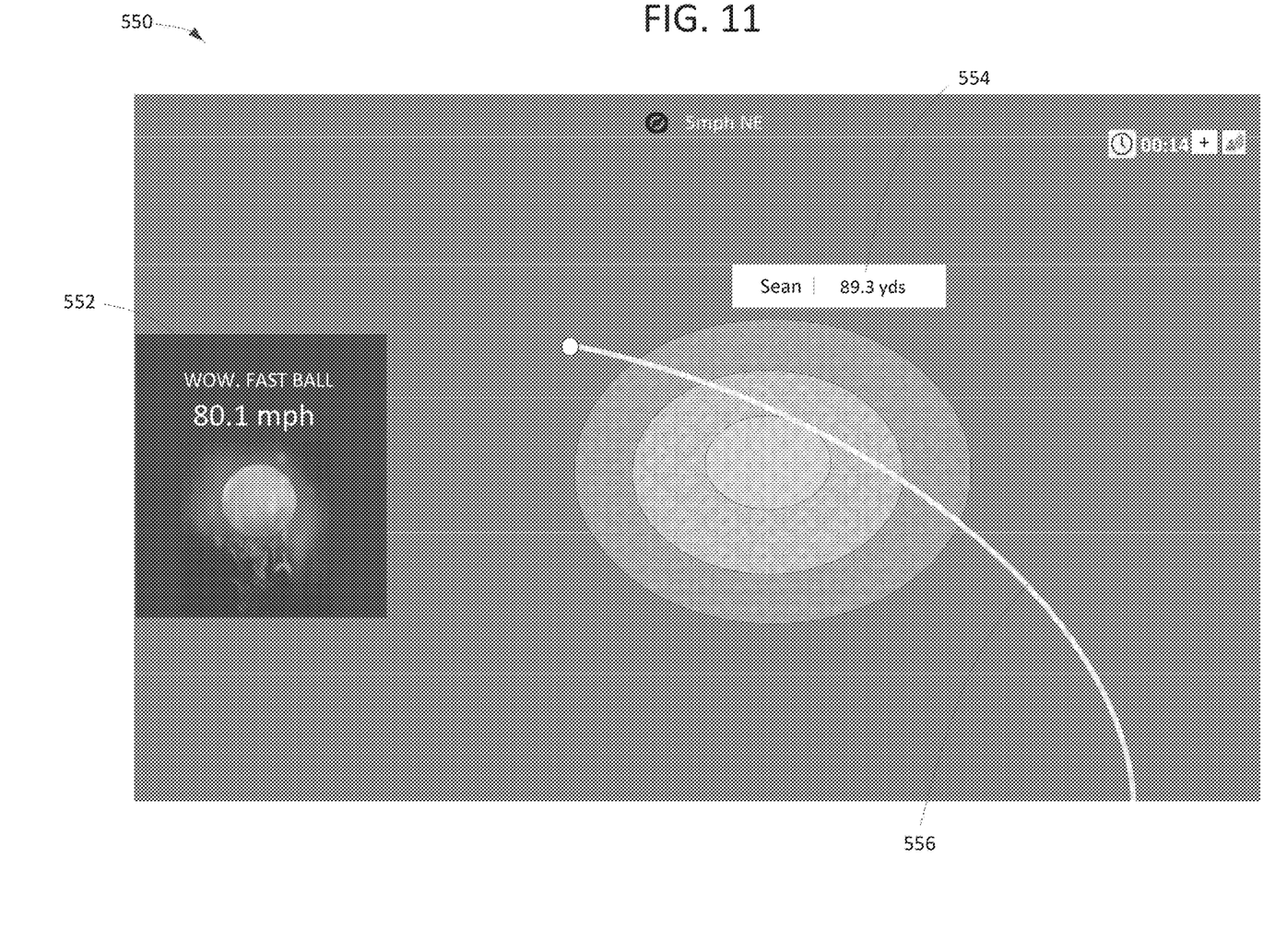
FIG. 11 depicts a screen shot of the flight path of an object and target within the virtual environment.

Turning to FIG. 11, depicted therein is a ball flight screen 550 that may be shown to the player on the monitor 400 during the flight of the ball and may also include information such as the speed of the ball 552, the exact location/distance 554 of the ball's landing and the flight path 556.

It is to be understood that even though numerous characteristics and advantages of various embodiments of the present invention have been set forth in the foregoing description, together with details of the structure and functions of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. It will be appreciated by those skilled in the art that the teachings of the present invention can be applied to other systems without departing from the scope and spirit of the present invention.

What is claimed is:

1. A game-play environment, comprising:
a physical tee box having a monitor;
a physical range surface extending from the tee box and having a plurality of physical markers; and
a physical golf ball;
wherein the monitor is configured to depict a virtual game-play environment, said game-play virtual environment comprising a plurality of virtual golf holes, each of said golf holes comprising a virtual tee box, a virtual fairway and a virtual green, said virtual game-play environment further comprising:
a virtual golf ball flight path of a virtual golf ball corresponding to an actual flight path of the physical golf ball from said tee box onto said range surface;
a plurality of visual components, wherein at least one of said visual components corresponds to features of said virtual golf holes, wherein one of the plurality of visual components is selected as a virtual target;
a plurality of visual cues, wherein each of the visual cues corresponds to a physical marker in the plurality of physical markers, wherein relative positions and distances between said plurality of physical markers are the same relative positions and distances depicted between said plurality of visual cues;
wherein said virtual game-play environment is configured to depict iterative targeting and game play from said virtual tee box to said virtual fairway and/or said virtual green of a desired physical marker corresponding to said visual cues, and wherein said virtual environment is further configured to depict each said virtual golf ball flight path during said iterative targeting and game play from said virtual tee box to said virtual fairway and said virtual green corresponding to said actual flight path of said physical golf ball relative to said desired physical marker; and wherein said monitor is further configured to redraw said virtual environment to depict a new position of said virtual golf ball after each successive iterative targeting and game play from said virtual tee box to said virtual fairway and/or said virtual green along each of said virtual golf holes;

wherein relative positions and distances between said desired physical markers are the same relative positions and distances depicted between said visual cues;

wherein the virtual game-play environment is configured to be selectively adjusted between each successive iterative targeting and game play from said virtual tee box to said virtual fairway and/or said virtual green along each of said virtual golf holes, where such adjustment between each successive iterative targeting and game play changes the proximity of a visual cue in the plurality of visual cues relative to a visual component within the plurality of visual components; and wherein the orientation of the virtual game-play environment depicted on the monitor can be selectively adjusted on the monitor between each successive iterative targeting and game play such that the position of the visual components within the virtual game-play environment changes with respect to the visual cues to selectively align the virtual target with the visual cue that corresponds to the physical target.

2. The game-play environment of claim 1 wherein the plurality of visual components comprise a virtual directional indicator, a virtual sand trap, a virtual water hazard, a virtual out of bounds marker, a virtual background feature, or a combination thereof.

3. The game-play environment of claim 1 wherein said virtual environment further comprises a virtual final resting place of the virtual golf ball corresponding to a relative position and distance from each of said plurality of visual cues that correspond to a relative position and distance of said physical golf ball from each of said plurality of physical markers of said range surface.

4. The game-play environment of claim 1 wherein the visual component comprises a playing card, a dart board, a bullseye, or a combination thereof.

5. The game-play environment of claim 1 wherein said virtual game-play environment further comprises a skill level select screen having a plurality of skill levels; wherein said virtual game-play environment is configured to dynamically change a target size of the virtual component based on a selected player skill level.

6. The game-play environment of claim 1 further comprising:
a data-storage device including instructions to perform the steps of:
determining whether the flight path of the virtual golf ball as depicted intersects a virtual target in the plurality of virtual cues; and
assigning a point value when an intersection occurs that is based upon the value of the intersected virtual cue; and
a processor configured to execute the instructions.

7. The game-play environment of claim 6 wherein the data-storage device includes additional instructions to perform the step of assigning a randomly generated point value when the flight path of the virtual golf ball does not intersect a virtual target in the plurality of virtual cues.

8. The game-play environment of claim 1 wherein said visual components further comprises:

a virtual landing strip positioned on a virtual range surface; and wherein said virtual-environment is configured to selectively rotate the depiction of said virtual landing strip relative to the plurality of visual cues, and wherein relative positions and distances between said plurality of physical markers are the same relative positions and distances depicted between said plurality of visual cues and said virtual landing strip.

9. The game-play environment of claim 8 wherein said virtual game-play environment further comprises a skill level select screen having a plurality of skill levels;

wherein said virtual game-play environment is configured to dynamically change a target size of the virtual landing strip based on a selected player skill level.

10. The game-play environment of claim 8 further comprising:
a data-storage device including instructions to perform the steps of:
determining when the final resting place of the golf ball as depicted is within the area of the virtual landing strip; and
assigning a point value based upon the position of the final resting place of the golf ball within the virtual landing strip; and
a processor configured to execute the instructions on the data-storage device.

11. A virtual game-play environment, comprising:
a virtual golf ball flight path of a virtual golf ball corresponding to an actual flight path of a physical golf ball from a physical tee box onto a physical range surface;
a first visual cue that corresponds to a first physical marker on a physical game-play surface;
a second visual cue that corresponds to a second physical marker on the physical game-play surface;
a visual component that is a golf course feature that does not exist on the physical game-play surface;
wherein the position and direction of the first visual cue relative to the second visual cue correspond to the position and direction of the first physical marker to the second physical marker;
wherein said virtual game-play environment comprises a plurality of virtual golf holes, each of said golf holes comprising a virtual tee box, a virtual fairway and a virtual green;
wherein said virtual game-play environment is configured to depict iterative targeting and game play from said virtual tee box to said virtual fairway and/or said virtual green, and wherein said virtual game-play environment is further configured to depict each said virtual golf ball flight path during said iterative targeting and game play from said virtual tee box to said virtual fairway and said virtual green corresponding to said actual flight path of said physical golf ball; and wherein said virtual game-play environment is further configured to be redrawn to depict a new position of said virtual golf ball after each successive iterative targeting and game play from said virtual tee box to said virtual fairway and/or said virtual green along each of said virtual golf holes;
wherein the virtual game-play environment is configured to be selectively adjusted between each successive iterative targeting and game play from said virtual tee box to said virtual fairway and/or said virtual green along each of said virtual golf holes, where such adjustment between each successive iterative targeting and game play changes the proximity of the first visual cue relative to the visual component, the proximity of the second visual cue relative to the visual component or the proximities of the first visual cue and the second visual cue relative to the visual component;

wherein relative positions and distances between said desired physical markers are the same relative positions and distances depicted between said first visual cue and/or said second visual cue; and wherein the orientation of the virtual game-play environment depicted on the monitor can be selectively adjusted between each successive iterative targeting and game play such that the position of the visual component within the virtual game-play environment changes with respect to the first visual cue and/or the second visual cue to selectively align a virtual target with the visual cue that corresponds to a player-selected physical target.

12. The virtual game-play environment of claim 11 wherein the visual component is a virtual golf hole, a virtual golf green, a virtual fairway, a virtual directional indicator, a virtual sand trap, a virtual water hazard, a virtual out of bounds marker, a virtual background feature, or a combination thereof.

13. The virtual game-play environment of claim 11 wherein the visual component is a playing card, a dart board, a bullseye, or a combination thereof.

14. The virtual game-play environment of claim 13 wherein said virtual game-play environment further comprises a skill level select screen having a plurality of skill levels; wherein said virtual game-play environment is configured to dynamically change a target size of the visual component based on a selected player skill level.

15. The virtual game-play environment of claim 11 wherein the position of the visual component is adjusted relative to the first visual cue and the second visual cue based on the position of the golf ball in the virtual environment.

16. The virtual game-play environment of claim 11 wherein said virtual environment further comprises a virtual final resting place of the virtual golf ball corresponding to a relative position and distance from each of said plurality of visual cues that correspond to a relative position and distance of said physical golf ball from each of said plurality of physical markers of said range surface.

17. A dual-environment golf game system, comprising:
a physical tee box having a monitor configured to be controlled by a player;
a physical range surface extending from the tee box and having a plurality of spaced apart physical markers, wherein one of the plurality of spaced apart physical markers is selected as a physical target by the player;
a physical golf ball;
a computer configured to run a game that is displayed on the monitor, wherein the game comprises:
a virtual environment comprising a plurality of visual components, wherein one of the plurality of visual components is selected as a virtual target by the player;
a plurality of visual cues, wherein each of the plurality of visual cues is associated with a separate one of the plurality of physical markers, and wherein the plurality of visual cues remains in fixed position within the virtual environment; and
wherein an orientation of the virtual environment that is displayed on the monitor can be selectively adjusted by the player such that the position of the plurality of visual components within the virtual environment changes with respect to the visual cues to permit the player to selectively align the virtual target displayed on the monitor with the visual cue that corresponds to the physical target.

18. The system of claim 17 wherein the virtual environment further comprises a plurality of virtual golf holes, each of said golf holes comprising a virtual tee box, a virtual fairway and a virtual green.

19. The system of claim 18 wherein the virtual environment further comprises a virtual golf ball flight path of a virtual golf ball corresponding to an actual flight path of the physical golf ball from the tee box onto the range surface.

20. The system of claim 19 wherein the virtual environment is configured to depict the iterative targeting and game play from the virtual tee box to the virtual fairway and/or the virtual green of the virtual golf holes corresponding to the visual cues, and wherein the virtual environment is further configured to depict each of the virtual golf ball flight paths during the iterative targeting and game play from the virtual tee box to the virtual fairway and the virtual green corresponding to the actual flight path of the physical golf ball relative to the physical target; and wherein the monitor is further configured to redraw the virtual environment to depict a new position of the virtual golf ball after each successive iterative targeting and game play from the virtual tee box to the virtual fairway and/or the virtual green along each of the virtual golf holes.

21. The system of claim 20 wherein the virtual environment is configured to be selectively adjusted between each successive iterative targeting and game play from the virtual tee box to the virtual fairway and/or the virtual green along each of the virtual golf holes, where such adjustment between each successive iterative targeting and game play changes the proximity of at least one of the visual cues of the plurality of visual cues relative to at least one of the visual components of the plurality of visual components.

22. The system of claim 18 wherein at least one of the visual components corresponds to features of the virtual golf holes, such features of the virtual golf holes not existing on the range surface; and wherein at least one of the visual components does not correspond to features of the virtual golf holes.

* * * * *